United States Patent [19]

Stephan et al.

[11] Patent Number: 4,734,279

[45] Date of Patent: Mar. 29, 1988

[54] COMBINATION OF IMMUNOGLOBULINS WITH THERAPEUTIC AGENTS

[75] Inventors: Wolfgang Stephan, Dreieich; Herbert Dichtelmuller, Sulzbach; Alexander Thrun; Hans Schleussner, both of Frankfurt am Main, all of Fed. Rep. of Germany

[73] Assignee: Biotest Pharma GmbH, Frankfurt am Main, Fed. Rep. of Germany

[21] Appl. No.: 756,672

[22] Filed: Jul. 19, 1985

[30] Foreign Application Priority Data

Jul. 20, 1984 [DE] Fed. Rep. of Germany ....... 3426903

[51] Int. Cl.⁴ .................... A61K 39/395; A61K 45/02
[52] U.S. Cl. ......................................... 424/85; 424/89; 424/92; 424/94.1; 424/101; 435/911; 514/2; 514/8; 514/885
[58] Field of Search ................... 424/85, 89, 92, 101, 424/94; 435/811; 514/2, 8, 885; 530/387

[56] References Cited

U.S. PATENT DOCUMENTS 4,412,990 11/1983 Lundblad et al. ................. 424/101

FOREIGN PATENT DOCUMENTS 98431A 1/1984 European Pat. Off. .
3329393A 2/1985 Fed. Rep. of Germany .

OTHER PUBLICATIONS

CA, #36952v, Pohwa et al, vol. 99, 1983, Persistent Cytomegalo-Virus Infection.
CA, #153382w, Frich et al, vol. 103, 1985, "Efficacy of Immunoglobulin in Gram-Negative Infection ... Mat".
CA, #173715k, Ng et al, vol. 93, 1980, Heterocomplexes of Interferons with Immunoglobulin ... Thereof.
Eckert et al., "Beitrag zur Effektivitat der Immunoglobuline bei der experimentellen Peritonitis", Langenbecks Arch. Chir. 351. 63–68 (1980).

Primary Examiner—John Kight
Assistant Examiner—Garnette D. Draper
Attorney, Agent, or Firm—Wegner & Bretschneider

[57] ABSTRACT

A compositon for treating diseases which comprises a therapeutically effective amount of an antibacterial, antiviral, or antimycotic agent, antitrypsin, antithrombin, interferon, or lysozyme, and an immunoenhancing amount of immunoglobulins IgG, IgM, and IgA, and a method of therapy of a mammal in need thereof are disclosed.

20 Claims, No Drawings

COMBINATION OF IMMUNOGLOBULINS WITH THERAPEUTIC AGENTS

The invention relates to the use of immunoglobulin preparations which, in addition to IgG, comprise other immunoglobulins, primarily on the IgM and IgA classes, in combination with another pharmacologically active agent as means for the treatment of disease.

In accordance with this invention, a composition for enhancing the activity of immunologically and pharmacologically active substances that contains a therapeutically effective mixture of a pharmaceutically active agent selected from the group consisting of antimicrobial agents, antitrypsin, and antithrombin, and an immunoenhancing combination of immunoglobulins IgG, IgM, and IgA is disclosed. The antimicrobial agents include antibacterial agents, antimycotic agents, interferon, fibronectin, and lysozyme. Also disclosed is a synergistic method of therapy of a mammal by administering a therapeutically effective amount of the above mixture.

The use of immunoglobulins in combatting infections is widespread. In the case of resistant germs, the use of immunoglobulins is frequently the only measure that promises success.

The synergistic action attainable through combined use of known immunoglobulin preparations and antibiotics has been described in numerous publications. Normal immunoglobulin preparations contain the immunoglobulin IgG and IgM.

The joint use of such immunoglobulin preparations with other pharmacologically active substances, such as fibronectin for example, has also been reported previously (European Patent Application 83105957.1).

Most recently there has been developed a human immunoglobulin preparation for intravenous use, which is designated as IGAM and which, besides the main constituent IgG, additionally contains immunoglobulins of the classes IgM and IgA. IGAM is obtained from the Cohn fraction III and consists of about 3700 mg IgG/100 ml of a 5 weight-% immunoglobulin, ca. 600 mg IgM/100 ml of such a solution, and ca. 820 mg IgA/100 ml of such a solution. In general, IGAM can be considered as being a mixture of IgG, IgM and IgA which comprises about 65 to 75 weight-% of IgG, about 8 to 20 weight-% of IgM and about 8 to 20 weight-% of IgA, based on the total amount of immunoglobulins.

Thanks to its IgM content, IGAM exhibits in the test of passive hemagglutination of substantially higher (sometimes more than 10 times higher) titer of antibodies than conventional immunoglobulin preparations which contain only IgG. The agglutination of the antigens (bacteria) leads to binding of the infection germs (clumping), hence to prevention of their spreading and a faster recognition and elimination by antigen-killing immune cells.

Until now, nothing has become known about the pharmacological effectiveness of IGAM in combined use with other drugs. It is now surprisingly found that a synergistic effect occurs when an immunoenhancing amount of IGAM is used jointly with certain other pharmacologically active preparations. These preparations, which together with IGAM exhibit a synergistic effect, are those containing antibiotics, tuftsin and other oligopeptides consisting of immunoglobulin chains, fibronectin, interferons, $\alpha_1$-antitrypsin, antithrombin and lysozyme.

The invention is explained in more detail below by means of exemplary embodiments.

In all cases, IGAM was used as an aqueous 5% immunoglobulin solution.

The combination preparations can be directly dissolved in the solutions of IGAM, while observing the requirements for intravenous use. The use of a mixture of IGAM with the relevant combination substance in powder form is also possible, the mixture being dissolved before the application.

It is also possible to incorporate the two substances into a vehicle, such as tablets or ointment.

The therapeutic application of the combination can be simultaneous, separate, or staggered in time. The immunoglobulin mixture and the second therapeutic agent can be administered either as a thoroughly commingled preparation or as separate independent preparations.

Tuftsin

Tuftsin is a tetrapeptide which is released from immunoglobulin G by enzymatic cleavage in the spleen and which thus occurs naturally in the body.

Tuftsin stimulates a number of immunological processes, including the activation of immunocompetent cells (increase of phagocytosis) and thereby also the accelerated destruction of the microorganisms that have invaded the organism.

These microorganisms are bound, agglutinated and prepared for phagocytosis by immunoglobulins. The phagocytosis (takeup of the microorganisms into the immunocompetent cells and the subsequent destruction) is stimulated by tuftsin. This promotes the two essential processes in the destruction of infectious agents.

Mice were infected with pseudomonas aeruginosa ($10^7$/animal intraperitoneally). Then an aqueous solution containing 0.5 mg of tuftsin dissolved in 0.5 ml of IGAM solution, was applied intravenously. 25 ml of the aqueous solution were applied per kg body weight. After 24 hours, all animals in an untreated control group had died, and likewise all animals that received only tuftsin. 44% of the animals were protected by the administration of immunoglobulin preparation, but 67% of the animals that received the combination of immunoglobulin and tuftsin were protected.

According to the invention, synthetically prepared oligopeptides can also be used together with the cited immunoglobulin preparations, especially for the therapy of infections and mycoses.

Cefamandole

Cefamandole was selected as a representative for the group of cephalosporin antibiotics.

In an experiment identical to the one with tuftsin, mice (21 animals per group) were infected with Salomonella typhimurium (i.p.) and then treated intravenously with cefamandole, IGAM or a mixture of IGAM and cefamandole (5 mg of immunoglobulin and 0.80 mg of cefamandole per animal). The survival of the animals was monitored for 17 days.

Result

In the untreated control group, 23% of the animals survived; 32% of the animals were protected by cefamandole along, 50% by IGAM alone. 78 percent of the animals were protected by the IGAM/cefamandole combination.

Moxalactam

Another antibiotic, Moxalactam was tested in combination with IGAM. AN injectable solution was prepared by dissolving 500 mg of Moxalactam in one (1) ml IGAM solution. In an experiment identical to the one with cefamandole, the same number of mice was infected with Escherichia coli (i.p.) and then treated intravenously with the injectable solution or IGAM plus Moxalactam (20 ml solution per kg body weight as a single dosis). The results were identical to those described for cefamandole.

Fibronectin

Fibronectin is a substance that occurs naturally in the organism. Bacteria are clumped together by fibronectin, whereby, on the one hand, the immunoglobulin-related agglutination is faciliated and, on the other hand, a premature consumption of immunoglobulins is prevented.

In an experiment identical to the test with tuftsin, animals infected with Pseudomonas aeruginosa were treated with a mixture of fibronectin (250 units/animal) and 25 mg of IGAM. The protective action of the combination was significantly better than that of the immunoglobulin alone. Fibronectin alone exhibited no protective action.

In another experiment, the same number of mice was infected with Staphylococcus aureus and first treated with an aqueous solution containing 500 units fibronectin/ml solution. The doses applied was 10,000 units fibronectin/kg body weight.

Thereafter, a 5 weight-% solution of IGAM was injected. The doses applied was 10 ml/kg body weight. The protective action was even better than in the case with Pseudomonas aeruginosa.

$\alpha_1$-antitrypsin ($\alpha_1$-AT)

$\alpha_1$-AT is an inhibitor of proteolytic activity. This proteolytic activity is related to bacterial infection and causes, among other things, inflammation at the site of a bacterial infection.

$\alpha_1$antitrypsin thus has an antiinflammatory effect. Hence too, a synergistic effect with respect to the therapeutic action is achieved by the binding (agglutination) of the bacteria by immunoglobulins and by the antiinflammatory action of $\alpha_1$-AT.

Antithrombin III (AT III)

AT III impedes the formation of blood clots (thromboses), which, on the one hand, impede the distribution of antiinfectious protective proteins (immunoglobulins) by blocking blood vessels, but, on the other hand, also promote the settling of microorganisms that have invaded.

In tests similar to those with tuftsin and cefamandole, a synergistic effect was observed in the joint application of IGAM and antithrombin III.

Interferons

Interferons are messenger substances which inform a neighboring cell that viruses have invaded a cell. The threatened cell reacts to these messenger substances by changing certain metabolic pathways so as to impede the multiplication of a virus that may have invaded.

Interferons thus protect a tissue from the spreading of and attack by viruses.

On the other hand, viruses can be bound by immunoglobulins and inactivated by means of complement. On the other hand, the protective mechanisms of neighboring cells are activated by interferons. That is, viruses searching for suitable cells to attack can be neutralized by immunoglobulins, and in addition the cells are stimulated by interferon to fight the viruses. The synergistic effect of interferon and immunoglobulins was established.

Lysozyme

Lysozyme occurs, among other places, in saliva and chicken eggs. The enzyme cleaves in the bacterial cell wall between N-acetylmuraminic acid and N-acetylglucosamine. In this manner, the cell wall structure can be broken up (lysis). The fragments of the bacteria lysed in this manner can be captured by immunoglobulins and supplied to the elimination process by immune cells.

In experiments identical to those with tuftsin and cefamandole, it was observed that a synergistic effect occurs when IGAM and lysozyme are used jointly.

What is claimed is:

1. A pharmaceutical composition comprising a therapeutically effective amount of
   (a) a therapeutic agent, wherein the agent is an antibacterial agent, tuftsin, antitrypsin, antithrombin, interferon, fibronectin, or lysozyme, and
   (b) an immunoenhancing amount of a mixture of immunoglobulins IgG, IgM, and IgA.
2. The composition of claim 1, wherein the therapeutic agent is an antibacterial agent.
3. The composition of claim 1, wherein the therapeutic agent is tuftsin.
4. The composition of claim 1, wherein the therapeutic agent is fibronectin.
5. The composition of claim 1, wherein the therapeutic agent is $\alpha$, $\beta$, or $\tau$-interferon.
6. The composition of claim 1, wherein the therapeutic agent is $\alpha$-antitrypsin.
7. The composition of claim 1, wherein the therapeutic agent is antithrombin III.
8. The composition of claim 1, wherein the therapeutic agent is lysozyme.
9. The composition of claim 2, wherein the antibacterial agent is a cephalosporin antibiotic.
10. The composition of claim 2, wherein the antibacterial agent is moxalactam.
11. A synergistic method of therapy of a mammal in need thereof which comprises administration of (a) a therapeutically effective agglutinizing amounts of immunoglobulins IgG, IgM, and IgA and (b) a therapeutically effective amount of a second therapeutic agent of the class consisting of antibacterial agents, tuftsin antitrypsin, antithrombin, fibronectin, interferon or lysozyme.
12. The method of claim 11, wherein the antibacterial agent is a cephalosporin antibiotic or moxalactam.
13. A method of claim 12 in which the immunoglobulin mixture and the second therapeutic agent are administered in a mixture.
14. A method of claim 12 in which the immunoglobulin mixture and the second therapeutic agent are administered in separate dosage units.
15. A method of claim 11 wherein the second therapeutic agent is tuftsin.
16. A method of claim 11 wherein the second therapeutic agent is fibronectin.
17. A method of claim 11 wherein the second therapeutic agent is $\alpha$, $\beta$, or $\gamma$-interferon.
18. A method of claim 11 wherein the second therapeutic agent is $\alpha_1$-antitrypsin.
19. A method of claim 11 wherein the second therapeutic agent is antithrombin III.
20. A method of claim 11 wherein the second therapeutic agent is lysozyme.

* * * * *